(12) United States Patent
Löbbert (10) Patent No.: US 11,525,817 B2
(45) Date of Patent: Dec. 13, 2022

(54) MEASURING ARRANGEMENT FOR DETERMINING AN OZONE CONTENT OF A MEASURED MEDIUM

(71) Applicant: Endress+Hauser Conducta GmbH+Co. KG, Gerlingen (DE)

(72) Inventor: Andreas Löbbert, Waldheim (DE)

(73) Assignee: Endress+Hauser Conducta GmbH+Co. KG, Gerlingen (DE)

(*) Notice: Subject to any disclaimer, the term of this patent is extended or adjusted under 35 U.S.C. 154(b) by 703 days.

(21) Appl. No.: 16/542,933

(22) Filed: Aug. 16, 2019

(65) Prior Publication Data
US 2020/0064325 A1 Feb. 27, 2020

(30) Foreign Application Priority Data
Aug. 22, 2018 (DE) .................. 10 2018 120 494.9

(51) Int. Cl.
*G01N 33/00* (2006.01)
*G01N 27/416* (2006.01)
(Continued)

(52) U.S. Cl.
CPC ....... *G01N 33/0039* (2013.01); *G01N 21/643* (2013.01); *G01N 21/77* (2013.01);
(Continued)

(58) Field of Classification Search
CPC .. G01N 33/0039; G01N 21/643; G01N 21/77; G01N 27/40; G01N 27/416;
(Continued)

(56) References Cited

U.S. PATENT DOCUMENTS

2004/0184962 A1* 9/2004 Klee .................. B01D 53/8675
422/83

FOREIGN PATENT DOCUMENTS

CN 108419353 A * 8/2018 ............... A61L 9/22
DE 2441857 A1 3/1976
(Continued)

OTHER PUBLICATIONS

Translation of CN 108419353A, Zhu, Ting, Aug. 17, 2018 (Year: 2018).*

(Continued)

*Primary Examiner* — Samuel P Siefke
*Assistant Examiner* — Henry H Nguyen
(74) *Attorney, Agent, or Firm* — Christopher R. Powers; Endress+Hauser (USA) Holding Inc.

(57) ABSTRACT

The present disclosure relates to a measuring arrangement for measuring an ozone content in a measured medium, including: a first sensor surface and a second sensor surface; a first cover element adjacent the first sensor surface and including an ozone binder that binds ozone without releasing oxygen or any species further reacting to form oxygen; a second cover element adjacent the second sensor surface and including an ozone converter that reacts with ozone to form oxygen; a measuring sensor configured to generate a first measurement signal dependent on the oxygen concentration at the first sensor surface and a second measurement signal dependent on the oxygen concentration at the second sensor surface; and an electronic evaluation unit configured to determine the ozone content in the measured medium based on the first and the second measurement signals.

18 Claims, 4 Drawing Sheets

(51) Int. Cl.
*G01N 21/64* (2006.01)
*G01N 27/40* (2006.01)
*G01N 21/77* (2006.01)

(52) U.S. Cl.
CPC ........... *G01N 27/40* (2013.01); *G01N 27/416* (2013.01); *G01N 2021/6432* (2013.01); *G01N 2021/775* (2013.01); *G01N 2021/7786* (2013.01)

(58) Field of Classification Search
CPC ..... G01N 2021/6432; G01N 2021/775; G01N 2021/7786; Y02A 50/20
See application file for complete search history.

(56) References Cited

FOREIGN PATENT DOCUMENTS

| | | |
|---|---|---|
| DE | 4222145 A1 | 1/1994 |
| DE | 102009049908 A1 | 4/2011 |
| DE | 102012213335 A1 | 2/2013 |
| JP | 07098291 A | 4/1995 |
| JP | 09015117 A | 1/1997 |
| JP | 2010223801 A * | 10/2010 |

OTHER PUBLICATIONS

Translation of JP2010223801A, Hayashida Shigeru, Oct. 7, 2010 (Year: 2010).*

* cited by examiner

MEASURING ARRANGEMENT FOR DETERMINING AN OZONE CONTENT OF A MEASURED MEDIUM

CROSS-REFERENCE TO RELATED APPLICATION

The present application is related to and claims the priority benefit of German Patent Application No. 10 2018 120 494.9, filed on Aug. 22, 2018, the entire contents of which are incorporated herein by reference.

TECHNICAL FIELD

The present disclosure relates to a measuring arrangement for determining an ozone content of a measured medium.

BACKGROUND

For determining an ozone content in a medium, a number of ozone sensors are known, for example electrochemical sensors, UV-absorption sensors, field-effect gas sensors, such as HSGFET (hybrid suspended-gate field-effect transistor) sensors, metal oxide resistance sensors, quartz microbalance sensors and optical sensors based on an indicator dye irreversibly reacting with ozone with a color change.

The most common sensors are amperometric sensors, which generally have a polymer membrane made of silicone. Amperometric sensors can themselves measure low ozone concentrations in the range of 10 ppb to 2 ppm but have the disadvantage of a high cross-sensitivity to other radical formers, such as chlorine dioxide or free chlorine (hypochlorous acid). An amperometric ozone measurement is therefore possible with sufficient accuracy only in media in which no other radical formers are present. Under certain circumstances, this may require a preparation of the measured medium before the ozone measurement is carried out. The service life of amperometric ozone sensors may be between 5 months and one year.

Another common method is UV/Vis absorption measurement, in which, for example, a mercury lamp is used as the light source. Sensors based on this method can measure very low ozone concentrations in the range of 1 ppb and have an overall measurement range of 0-10 ppm. Such sensors generally have a lifespan of several years. However, due to the high energy requirements for operating the mercury lamp, these optical sensors consume substantially more energy than amperometric ozone sensors. Measuring devices known from the prior art and based on absorption measurement for determining ozone concentration cannot be used as in-line sensors so that monitoring a measured medium regularly requires sampling. As a rule, the known devices are maintenance-intensive and require more space than electrochemical sensors.

Metal oxide resistance sensors can also be used to measure ozone concentrations. These sensors are based on the ability of metal oxides to convert gases into ions or complexes by dissociation with release of electrons. Common metal oxides used in these sensors are, for example, tin oxide, titanium oxide, zinc oxide and cerium oxide. The change in the resistance of the metal oxide is used for gas detection. However, these sensors have only a low selectivity.

HSGFET sensors are suitable for measuring ranges of ozone concentration between 20 and 100 ppb. However, known HSGFET sensors show a disadvantageous drift of the gate voltage of the field-effect transistor, which currently stands in the way of commercial use of these sensors. Quartz microbalance sensors for ozone measurement are currently only of academic interest.

Optical sensors based on quenching the fluorescence of an indicator dye by interaction with ozone molecules cannot currently be used for ozone measurement due to known problems, such as photobleaching of the indicator dye and aging of the polymer matrix containing the indicator dye. Only optical sensors based on a dye reacting irreversibly with ozone and usable only for a single measurement have become known. Continuous, permanent monitoring of the ozone content of a measured medium is therefore not possible with the optical sensors currently known in the prior art and based on fluorescence quenching.

SUMMARY

The object of the present disclosure is to provide a measuring arrangement which is suitable for continuously and permanently monitoring an ozone content in a measured medium. The measuring arrangement should preferably also be suitable for performing in-line measurements, that is to say, measurements taken directly in a measured medium that is guided in a fluid line or held in a container of a process installation.

This aim is achieved by the measuring arrangement according to claim 1 and the method according to claim 18. Advantageous embodiments are listed in the dependent claims.

The measuring arrangement according to the present disclosure for measuring an ozone content in a measured medium includes:

a first sensor surface and a second sensor surface;

a first cover element arranged above the first sensor surface and comprising an ozone binder, namely a substance which binds ozone without releasing oxygen or any species further reacting to form oxygen, wherein a side of the first cover element facing away from the first sensor surface is designed to contact the measured medium, and wherein the first cover element is permeable at least to oxygen;

a second cover element arranged above the second sensor surface and comprising an ozone converter, namely a substance that reacts with ozone to form oxygen, wherein a side of the second cover element facing away from the second sensor surface is designed to contact the measured medium, and wherein the second cover element is permeable at least to oxygen;

a measuring sensor designed to generate a first measurement signal dependent on the oxygen concentration present at the first sensor surface and a second measurement signal dependent on the oxygen concentration present at the second sensor surface; and an evaluation circuit, in particular an electronic evaluation unit, that is designed to determine a value of a measured variable representing the ozone content in the measured medium on the basis of the first and the second measurement signals.

The measuring arrangement thus detects the oxygen concentrations present at the sensor surfaces to determine the ozone content in the measured medium. Only the oxygen contained in the measured medium arrives at the first sensor surface, while the ozone bound in the first cover element does not enter the first measurement signal. Both the oxygen contained in the measured medium and the oxygen formed by converting the ozone penetrating the second cover element reach the second sensor surface. The difference between the oxygen concentration present at the first sensor surface and the oxygen concentration present at the second sensor surface is therefore a measure of the ozone concentration converted in the second cover element and thus also of the ozone concentration present in the measured medium. In this way, the ozone concentration present in the measured medium can be determined by means of a conventional measuring sensor for determining an oxygen concentration, such as a conventional optical measuring sensor based on quenching the fluorescence of an indicator substance (e.g., fluorophore), or an amperometric measuring sensor. Conventional amperometric or optical measuring sensors for selective oxygen measurement are known in the prior art and are routinely used for permanently monitoring measured media, in particular in process analysis. In the manner described, a measuring arrangement for ozone measurement is thus provided and is sufficiently selective and has the properties required for permanently monitoring a measured medium.

Since the ozone binder contained in the first cover element binds ozone penetrating into the first cover element and the ozone converter contained in the second cover element converts into oxygen the ozone penetrating into the second cover element, no reactive ozone reaches the first and second sensor surfaces directly. Irreversible reactions of the sensor surface or of substances present in or on the sensor surface, e.g. membrane materials and/or indicator substances, with ozone and aging processes associated therewith are therefore considerably reduced. An adequate service life of the measuring arrangement is therefore ensured.

The substance forming the ozone binder may be formed from a single chemical compound or from a plurality of different chemical compounds. The substance forming the ozone converter can also be composed of a single chemical compound or of a plurality of chemical compounds.

In a possible embodiment, the measuring sensor may include:
at least one first and one second light source;
at least one light receiver;
a membrane that includes the first sensor surface and the second sensor surface and in which an oxygen indicator substance is immobilized;
optical waveguides connecting the first light source and the light receiver to a region of the membrane covered by the first sensor surface; and
optical waveguides connecting the second light source and the light receiver to a region of the membrane covered by the second sensor surface.

The at least one light receiver can be configured to convert into electrical signals light received via the optical waveguides. The measuring sensor may further include a measuring circuit configured to excite the first and second light sources sequentially or alternately to emit measuring light, and which is further designed to generate the first and second measurement signals from electrical signals of the at least one light receiver. The measuring circuit can form part of the evaluation circuit or can be connected to the evaluation circuit for communication purposes.

In a further embodiment, the measuring sensor may include:
at least one light source;
at least one first light receiver and one second light receiver;
a membrane that includes the first sensor surface and the second sensor surface and in which an oxygen indicator substance is immobilized;
optical waveguides connecting the light source and the first light receiver to a region of the membrane covered by the first sensor surface; and
optical waveguides connecting the light source and the second light receiver to a region of the membrane covered by the first [sic: second] sensor surface.

In this further embodiment, too, the measuring sensor may include a measuring circuit configured to excite the at least one light source to emit measuring light and further configured to generate the first measurement signal from electrical signals of the first light receiver and to generate the second measurement signal from electrical signals of the second light receiver. The measuring circuit can form part of the evaluation circuit or can be connected to the evaluation circuit for communication purposes.

In these embodiments, the measuring arrangement can have a membrane formed from one or more layers, the surface of said membrane facing the measured medium being divided into at least two sensor surfaces, namely the first and the second sensor surfaces. An oxygen indicator, for example a dye which can be excited to luminescence (fluorescence or phosphorescence), also referred to as a luminophore or fluorophore, the luminescence of which is attenuated by interaction with oxygen molecules (luminescence quenching, e.g. fluorescence quenching), can be contained in one or more layers of the membrane.

Advantageously, a first region of the membrane arranged adjacent to the first sensor surface is hermetically separated from a second region of the membrane arranged adjacent to the second sensor surface by, for example, a separator running between these regions. The separation, for example the separator, can divide the membrane over its full height or, if the membrane is composed of a plurality of layers, divide only one or some layers, for example only an indicator layer of the membrane, into separate regions.

In the arrangement in such an embodiment, the optical waveguides can be routed in such a way that the indicator in the region of the first sensor surface and the indicator in the region of the second sensor surface can be excited to luminescence alternately (first embodiment) or simultaneously (second embodiment) by irradiating measuring light. In the first embodiment, the luminescence light from the region of the first sensor surface can be guided via a first optical waveguide to the light receiver, and the luminescence light from the region of the second sensor surface can be guided via a second optical waveguide to the light receiver. In the second embodiment, the luminescence light from the first region can be guided via a first optical waveguide to the first light receiver and the luminescence light from the second region can be guided via a second optical waveguide to the second light receiver.

In yet another embodiment, the measuring sensor can include:
at least one light source;
at least one light receiver;
a first membrane including the first sensor surface and a second membrane including the second sensor surface, an oxygen indicator substance being immobilized in the first and second membranes;
one or more first optical waveguides connecting the light source and the light receiver to the first membrane; and
one or more second optical waveguides connecting the light source and the light receiver to the second membrane.

In such an embodiment, the light receiver can also be configured to convert into electrical signals the light received via the one or more optical waveguides. The measuring sensor can include a measuring circuit configured to excite the at least one light source to emit measuring light and which is further configured to generate the first and the second measurement signals from electrical signals of the at least one light receiver.

In such an embodiment, the first membrane may be formed from one or more layers, wherein at least one of the layers comprises an oxygen indicator, for example a luminophore as described above with reference to the first embodiment. The second membrane may be formed like the first membrane. The first and second membranes may be arranged in a common housing, and the at least one light source may be used to excite the luminescence of the oxygen indicator contained in the first and second membranes. Accordingly, the one or more first and second optical waveguides may direct measuring light of the light source onto the first and second membranes in order to excite the luminescence of the oxygen indicator. Luminescence light from the region of the first and second membranes can be guided to the light receiver via the optical waveguides. In the arrangement in this embodiment, the optical waveguides can be routed in such a way that the indicator in the first membrane and the indicator in the second membrane can be excited to luminescence simultaneously or alternately by irradiating measuring light, and that the luminescence light from the region of the first sensor surface is guided via a first optical waveguide to the light receiver and that the luminescence light from the region of the second sensor surface is guided via a second optical waveguide to the light receiver so that the luminescence light that results in the generation of the first measurement signal is guided separately from the luminescence light that results in the generation of the second measurement signal.

In yet a further embodiment, the measuring sensor can include: at least one first light source and at least one second light source; at least one first light receiver and at least one second light receiver; a first membrane comprising the first sensor surface and a second membrane comprising the second sensor surface, an oxygen indicator substance being immobilized in the first and second membranes; one or more first optical waveguides connecting the first light source and the first light receiver to the first membrane; and one or more second optical waveguides connecting the second light source and the second light receiver to the second membrane.

The first light receiver may be designed to convert light received via the one or more first optical waveguides into first electrical signals, and the second light receiver may be designed to convert light received via the second or the plurality of second optical waveguides into second electrical signals, and wherein the measuring sensor has a measuring circuit which is designed to generate the first measurement signal from the first [electrical] signals and the second measurement signal from the second electrical signals.

The first membrane, the first light source, the first light receiver, and the first optical waveguides may be housed in a first housing. The second membrane, the second light source, the second light receiver, and the second optical waveguides may be housed in a second housing separate or separable from the first housing. The measuring circuit can be arranged outside the first and second housings, in particular also at a distance from the first and second housings. The measuring circuit may also be divided into two components, wherein a first component of the measuring circuit, which is designed to excite the first light source and to generate the first measurement signal, is arranged in the first housing and a second component of the measuring circuit, which is designed to excite the second light source and to generate the second measurement signal, is arranged in the second housing. All mentioned components of the measuring sensor can also be accommodated in a common housing which can be subdivided into a plurality of chambers. The measuring circuit or the individual parts of the measuring circuit can form part of the evaluation circuit or can be connected to the evaluation circuit for communication purposes.

In a fifth possible embodiment, the measuring sensor can include: a first membrane comprising the first sensor surface and a second membrane comprising the second sensor surface, wherein the first and second membranes are permeable to oxygen; a first electrolyte chamber, which is closed off by the first membrane and filled with a first electrolyte and in which a first working electrode and a first counter electrode are arranged; a second electrolyte chamber, which is closed off by the second membrane and filled with a second electrolyte and in which a second working electrode and a second counter electrode are arranged; and a measuring circuit designed to generate first electrical signals representative of a current passing through the first electrolyte at a polarization voltage applied between the first working electrode and the first counter electrode and to generate the first measurement signal from the first electrical signals, and designed to generate second electrical signals representative of a current passing through the second electrolyte at a polarization voltage applied between the second working electrode and the second counter electrode and to generate the second measurement signal from the second electrical signals.

The measuring circuit can form part of the evaluation circuit or can be connected to the evaluation circuit for communication purposes.

In all of the embodiments described above, the evaluation circuit can be, for example, a circuit of a conventional measuring transducer of process measurement technology. This measuring transducer can comprise a housing containing input means, via which a user can input commands or parameters, as well as display means by means of which measured values or other information can be displayed. The measuring transducer can also be designed as a compact measuring transducer. In this case, the measuring transducer comprises a housing in which a transducer circuit is accommodated which processes the measurement signals and forwards them via a cable and/or by radio but in which no separate input or display means are provided. The information transmitted by cable or radio, in particular measured values, can be received, optionally processed and displayed by an external operating device, for example a portable computer, a tablet, a smart phone or another smart device.

In all of the embodiments described above, the first cover element can take the form of a layer arranged above the first sensor surface and the second cover element can take the form of a layer arranged above the second sensor surface. A hygiene layer provided for contact with the measured medium can be arranged above the layer forming the cover element. This hygiene layer may be formed of a hydrophilic or superhydrophilic material.

The first cover element can be designed as a capsule, in particular a detachable capsule, upstream of the first sensor surface or as a compartment, arranged above the first sensor surface, of a capsule, in particular a detachable capsule, upstream of the first sensor surface. The second cover element can also be designed as a capsule, in particular a detachable capsule, upstream of the second sensor surface or as a compartment, arranged above the second sensor surface, of a capsule, in particular a detachable capsule, upstream of the second sensor surface.

The capsule may comprise a compartment containing the ozone binder and/or a compartment containing the ozone scavenger, wherein the compartment or each compartment has a media-contacting front wall and a rear wall contacting the first sensor surface and/or the second sensor surface, and wherein the front wall and the rear wall may have a liquid transfer feature.

The liquid transfer feature can be formed by a fiber diaphragm or by a ceramic diaphragm or by a gap or by a cut or by a fluid-permeable organic or inorganic membrane.

In an advantageous embodiment, the capsule is accommodated in a cap which is connected, in particular detachably, to a housing part of the measuring sensor.

If the measuring sensor is designed as an optical measuring sensor based on the principle of luminescence quenching, as in the case of the first, second, third and fourth described embodiments, the membrane comprising the first and/or the second sensor surface can be applied to a substrate. On its side facing the substrate, the membrane can optionally comprise an adhesion-promoter layer which improves adhesion to the substrate. The membrane may additionally comprise an optical isolation layer and/or a reflection layer and/or a diffusion layer. These layers may be arranged between the cover element and the layer containing the indicator.

The ozone binder may comprise at least one unsaturated compound, in particular an unsaturated hydrocarbon compound, for example an alkene, an alkyne or a vinyl, which forms an ozonide with ozone, and a reagent for the oxidative or reductive preparation of the ozonide, for example a reducing agent, such as zinc, iron, dimethyl sulfoxide, or an oxidizing agent, such as a peroxide.

The ozone converter may comprise an alkaline buffer, in particular an alkaline buffer solution or an alkaline, buffered solid electrolyte, or a reducing agent, for example a thiol, or a salt which reacts with ozone to form oxygen, for example an alkali halide salt or an alkali pseudohalide salt (—CN, —N3, —OCN, —NCO, —CNO, —SCN, —NCS, —SeCN), or an enzyme, for example superoxide dismutase (SOD) containing Cu or Zn.

The first cover element may advantageously comprise an aldehyde binder in addition to the ozone binder. The aldehyde binder may serve to inhibit uncontrolled subsequent reactions of products or intermediates formed during the chemical binding of the ozone. Suitable aldehyde binders are polar groups, such as alcohol or amine groups, which may be bound to molecules contained in the cover element or to a polymer matrix.

The second cover element may comprise a radical scavenger in addition to the ozone converter. This can advantageously prevent the second measurement signal from being affected by radicals, in particular oxygen radicals, interacting with the second sensor surface. In addition, aging of the sensor surface or of indicator substances present in the region of the sensor surface can be counteracted by quenching radicals. Examples of suitable radical scavengers are thiols or sterically hindered amines or phenols.

The entire measuring arrangement according to one of the embodiments described here can take the form of a cohesive unit. In particular, the measuring sensor, the membrane(s) and the cover elements can be inseparably connected to one another and thus form such a cohesive unit. This unit can be intended for single use, i.e. as a disposable sensor. If the membrane or the ozone binder or ozone converter contained in the cover elements is consumed or aged to such an extent that sufficient measurement accuracy is no longer given, the whole unit is in this case taken out of service.

The present disclosure also includes a method for measuring an ozone content in a measured medium, including: bringing a first sensor surface covered by a first cover element into contact with a measured medium; bringing a second sensor surface covered by a second cover element into contact with the measured medium; converting ozone entering the first cover element from the measured medium into oxygen by means of a chemical reaction with an ozone converter contained in the cover element; detecting a first measurement signal dependent on an oxygen concentration present at the first sensor surface; binding ozone entering the second cover element from the measured medium to an ozone binder contained in the second cover element; detecting a second measurement signal dependent on an oxygen concentration present at the second sensor surface; and determining from the first and the second measurement signals a measured value of the ozone content in the measured medium.

Determining the measured value may include the following steps: determining from the first measurement signal a first measured value representing an oxygen concentration at the first sensor surface; determining from the second measurement signal a second measured value representing an oxygen concentration at the second sensor surface; determining the measured value from a difference between the first and the second measured values.

The subject-matter of the present disclosure also relates to a sensor spot for use in a measuring arrangement according to one of the embodiments described above or in a method according to one of the embodiments described above. The sensor spot includes at least one first sensor surface, a first cover element arranged above the first sensor surface and including an ozone binder or an ozone converter, wherein a side of the first cover element facing away from the first sensor surface is designed to contact a measured medium, and wherein the first cover element is permeable to oxygen so that oxygen from the side of the first cover element facing away from the first sensor surface reaches the first sensor surface.

The sensor spot may further include a second sensor surface and a second cover element arranged above the second sensor surface, wherein the first cover element comprises an ozone binder, the second cover element comprises an ozone converter, and wherein a side of the second cover element facing away from the second sensor surface is designed to contact the measured medium, wherein the second cover element is permeable to oxygen so that oxygen reaches the second sensor surface from the side of the second cover element facing away from the second sensor surface.

The first and/or the second cover element can be designed as described above with reference to the measuring arrangement. In particular, the first cover element can take the form of a layer arranged above the first sensor surface and the second cover element can take the form of a layer arranged above the second sensor surface. It is also possible for the first cover element to be designed as a capsule, in particular detachably connected upstream of the first sensor surface, or as a compartment of such a capsule, and for the second cover element to be designed as a capsule, in particular detachably connected upstream of the second sensor surface, or as a compartment of such a capsule. The capsules or compartments can be designed as described above in connection with the measuring arrangement.

The sensor spot can include a membrane which is formed from one or more layers and whose surface facing the measured medium is divided into two sensor surfaces, namely the first and the second sensor surfaces. Otherwise, the membrane may be designed as described above with reference to measuring arrangement. The membrane can be applied to a substrate which is transparent to measuring light and serves as a stable carrier.

Advantageously, a first region of the membrane arranged adjacent to the first sensor surface is hermetically separated from a second region of the membrane arranged adjacent to the second sensor surface by, for example, a separator running between these regions. The first region may, for example, be arranged in the membrane below the first sensor surface and the second region may be arranged in the membrane below the second sensor surface. The separation, for example the separator, can divide the membrane over its full height or, if the membrane is composed of a plurality of layers, divide only one or some layers, for example only an indicator layer of the membrane, into separate regions. An oxygen indicator substance is immobilized in each of the first and second regions of the membrane.

The sensor spot can include a cap-shaped housing, hereinafter referred to as a cap, in which a membrane including at least the first sensor surface is accommodated. The membrane may be accommodated on a substrate. In addition, the first cover element upstream of the first sensor surface can also be arranged in the cap. The first cover element can be designed as a layer arranged above the first sensor surface or as a capsule or compartment, as described above. At one end, the cap can have an opening via which a front side of the membrane comprising at least the first sensor surface, or at least the first cover element arranged above the first sensor surface, can be brought into contact with a measured fluid located outside the cap. If the membrane has a second sensor surface and a second cover element arranged above the second sensor surface, the opening is designed in such a way that the first and the second sensor surface or the first and the second cover element can be brought into contact with the measured fluid via said opening. At its other end opposite the end comprising the opening, the cap can have fastening means, for example a thread, suitable for fastening the cap to a housing of a measuring sensor, in particular of an optical or amperometric measuring sensor.

The subject-matter of the present disclosure also relates to a capsule for use in a measuring arrangement according to one of the embodiments described above. The capsule may include a housing in which at least a first compartment containing an ozone binder or an ozone converter is formed, and which comprises a liquid transfer feature in a first wall intended for contact with a first sensor surface of a measuring arrangement, and which further comprises a second liquid transfer feature in a second wall opposite the first wall.

A second compartment may be formed in the housing of the capsule, wherein an ozone binder is contained in the first compartment and an ozone converter is contained in the second compartment, and wherein the second compartment comprises a liquid transfer feature in a first wall intended for contact with a second sensor surface of the measuring arrangement and further includes a second liquid transfer feature in a second wall opposite the first wall.

Otherwise, the capsule can be designed as described with reference to the measuring arrangement.

In an advantageous embodiment, the capsule includes an outer housing in the form of a cap in which the capsule is accommodated and which has at a first end an opening via which the capsule can be brought into contact with a measured medium and which at a second end opposite the first end has fastening means, for example a thread, suitable for fastening the capsule to a housing of a measuring sensor, in particular of an optical or amperometric measuring sensor.

BRIEF DESCRIPTION OF THE DRAWINGS

The present disclosure is explained in further detail below on the basis of the exemplary embodiments shown in the figures. They show.

DETAILED DESCRIPTION

Figure 1:
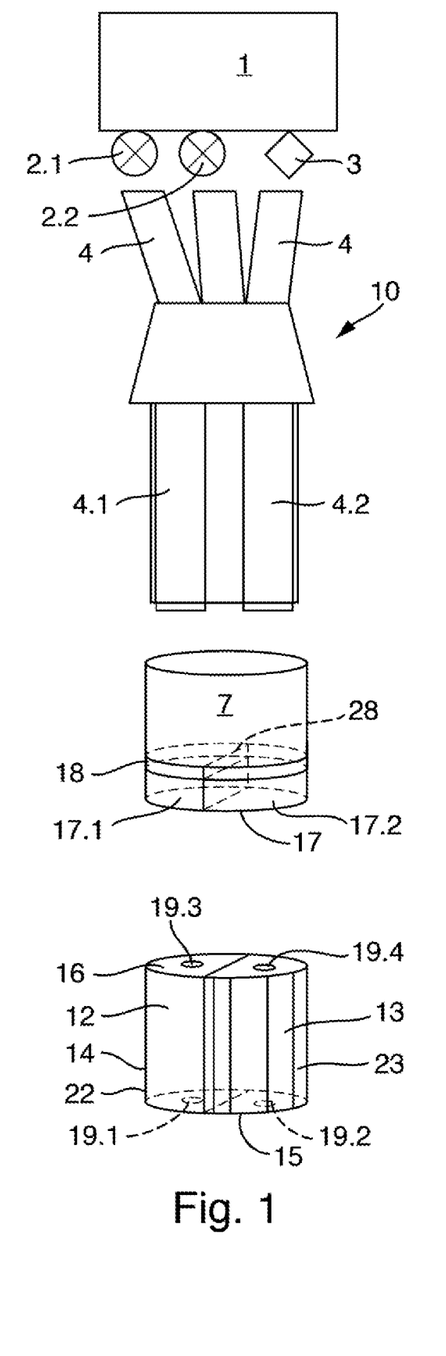
FIG. 1 shows a schematic representation of components of a measuring arrangement for measuring an ozone concentration in a measured medium according to an exemplary embodiment.

FIG. 1 schematically illustrates a measuring arrangement 10 for measuring an ozone concentration in a liquid or gaseous measured medium according to a first exemplary embodiment. The measuring arrangement 10 includes a measuring circuit 1, two light sources 2.1, 2.2 connected to the measuring circuit 1 and a light receiver 3 connected to the measuring circuit 1. The measuring circuit 1 is designed to alternately excite the light sources 2.1, 2.2 to emit measuring light, and also to receive and process electrical signals of the light receiver 3. Furthermore, the measuring arrangement 10 includes a membrane 7 that has at least one indicator layer 18 containing an oxygen indicator. The indicator layer 18 may, for example, be formed of a polymer, such as a silicone-based polymer, in which the oxygen indicator is immobilized. The oxygen indicator can be, for example, a luminophore, for example a fluorophore, which can be excited to luminescence or fluorescence by light emitted by the light sources 2.1, 2.2 and whose luminescence or fluorescence is attenuated (e.g., quenched) by interaction with oxygen molecules.

The measuring arrangement 10 further includes a capsule 14, the front side 15 of which is intended for contact with the measured medium and whose rear side 16 covers the front side 17 of the membrane 7 facing the capsule 14. In the present exemplary embodiment, the capsule 14 is divided into two compartments 12 and 13. The surface region of the front side 17 of the membrane 7 arranged adjacent the first compartment 12 forms a first sensor surface 17.1; the surface region of the front side 17 of the membrane 7 arranged adjacent the second compartment 13 forms a second sensor surface 17.2 of the measuring arrangement 10. During operation of the measuring arrangement 10, the capsule 14 is arranged upstream of the sensor surfaces 17.1, 17.2 of the membrane 7 in such a way that the rear side 16 covers the sensor surfaces 17.1, 17.2 and rests against them. The first compartment 12 thus forms a first cover element 22 covering the first sensor surface 17.1; the second compartment 13 correspondingly forms a second cover element 23 covering the second sensor surface 17.2. The cover elements 22, 23 completely cover the sensor surfaces 17.1, 17.2 with respect to a measured medium contacting the front side 15 of the capsule 14.

The measuring arrangement 10 includes an optical waveguide bundle consisting of optical waveguides 4, 4.1, 4.2 which connect the light sources 2.1, 2.2 and the light receiver 3 to a region of the membrane 7 covered by the first sensor surface 17.1 and to a region of the membrane 7 covered by the second sensor surface 17.2. Measuring light from the first light source 2.1 emerging from the optical waveguides 4.1 falls onto the region of the membrane 7 covered by the first sensor surface 17.1. Measuring light from the second light source 2.2 emerging from the optical waveguides 4.2 falls onto the region of the membrane 7 covered by the second sensor surface 17.2. Luminescence light arising in the indicator layer 18 adjacent the first sensor surface 17.1 reaches the light receiver 3 via the optical waveguides 4.1, 4. Luminescence light arising in the indicator layer 18 adjacent the second sensor surface 17.2 correspondingly reaches the light receiver 3 via the optical waveguides 4.2, 4. Said light receiver 3 is designed to convert received fluorescent light into electrical signals. In at least one embodiment, the region of the indicator layer 18 arranged adjacent the first sensor surface 17.1 is hermetically separated from the region of the indicator layer 18 arranged adjacent the second sensor surface 17.2, for example by a separator made of a fluid-impermeable material, to prevent oxygen or other substances from passing between the two regions.

The first compartment 12 of the capsule 14 contains an ozone binder, i.e., a substance that binds ozone without thereby releasing oxygen or any species that reacts further with oxygen. The second compartment 13 contains an ozone converter, i.e., a substance that reacts with ozone to form oxygen. In its wall forming the front side 15, the capsule 14 has a first liquid transfer feature 19.1 opening into the first compartment 12 and a second liquid transfer feature 19.2 opening into the second compartment 13. In its wall forming the rear side 16 of the capsule 14, the capsule 14 has a third liquid transfer feature 19.3 opening into the first compartment 12 and a fourth liquid transfer feature 19.4 opening into the second compartment 13. In the present embodiment, the liquid transfer features 19.1, 19.2, 19.3, 19.4 take the form of openings passing through walls. They can also take the form of diaphragms, liquid-permeable membranes, gaps or cuts.

Oxygen and ozone pass from the measured medium via the first liquid transfer feature 19.1 into the first compartment 12. There, ozone is bound by the ozone binder so that only oxygen, but not ozone, passes from the measured medium via the third liquid transfer feature 19.3 to the first sensor surface 17.1 and into the membrane 7. Oxygen and ozone from the measured medium pass via the second liquid transfer feature 19.2 into the second compartment 13. There, ozone is converted into oxygen by the ozone converter so that both the oxygen from the measured medium and the oxygen formed by reaction with the ozone converter reach the second sensor surface 17.2 via the fourth liquid transfer feature 19.4.

In the first compartment 12 and in the second compartment 13, the capsule 14 can optionally contain fibers, for example inorganic fibers, which accelerate by capillary forces a substance transfer from the first and second liquid transfer features 19.1, 19.2 or from the first and second compartments 12 and 13 to the first and second sensor surfaces 17.1, 17.2. The response time of the measuring arrangement 10 can thus be reduced.

The concentration of ozone in the measured medium can be determined with the measuring arrangement 10 by means of two luminescence measurements. In a first measurement, the first light source 2.1 is excited by the measuring circuit 1 to emit measuring light, said light being conducted via the optical waveguides 4, 4.1 to the first sensor surface 17.2. The measuring light excites to luminescence the indicator contained in the indicator layer 18 of the membrane 7 in the region adjacent the first sensor surface 17.1. This luminescence is attenuated as a function of the oxygen concentration present at the first sensor surface 17.1. The luminescence light passes via the optical waveguides 4.1, 4 to the light receiver 3 which converts the received light into a first electrical measurement signal. The first measurement signal is therefore a measure of the oxygen concentration present at the first sensor surface 17.1, which in turn is a measure of the oxygen concentration present in the measured medium.

In a second measurement, the second light source 2.2 is excited by the measuring circuit 1 to emit measuring light, said light being conducted via the optical waveguides 4, 4.2 to the second sensor surface 17.2. The measuring light excites to luminescence the indicator contained in the indicator layer 18 of the membrane 7 in the region below the second sensor surface 17.2. This luminescence is attenuated as a function of the oxygen concentration present at the second sensor surface 17.2. The luminescence light passes via the optical waveguides 4.2, 4 to the light receiver 3, which converts the received light into a second electrical measurement signal. The second measurement signal is a measure of the oxygen concentration present at the second sensor surface 17.2, which in turn is a measure of the sum of the oxygen concentration present in the measured medium and the ozone concentration (via the oxygen formed by reaction with the ozone converter) present in the measured medium.

The measuring circuit 1 is designed to carry out the two described luminescence measurements and to process the first and the second measurement signal to determine a value of the ozone concentration in the measured medium on the basis of these signals. For this purpose, the measuring circuit 1 can contain a processor, a data memory and a computer program stored in the data memory and executable by the processor to detect and process the measurement signals. Furthermore, the measuring circuit 1 can include means for the analog/digital conversion of analog measurement signals generated by the receiver 3 into digital signals which can be processed by the processor.

To determine the ozone concentration in the measured medium, the measuring circuit 1 or the computer program can be designed, for example, to determine a first measured oxygen value from the first measurement signal and to determine a second measured oxygen value from the second measurement signal, to form a difference from the first and the second measured oxygen values, and to determine a value of the ozone concentration in the measured medium on the basis of the difference. The stoichiometry of the chemical reaction, by means of which the ozone converter converts ozone into oxygen, must be taken into account here.

In an alternative method for determining the ozone concentration in the measured medium, the measuring circuit 1 can first form a difference between the first and the second measurement signals and determine a measured value of the ozone concentration in the measured medium from the difference based, for example, on a stored calibration function or calibration table.

Figure 2:
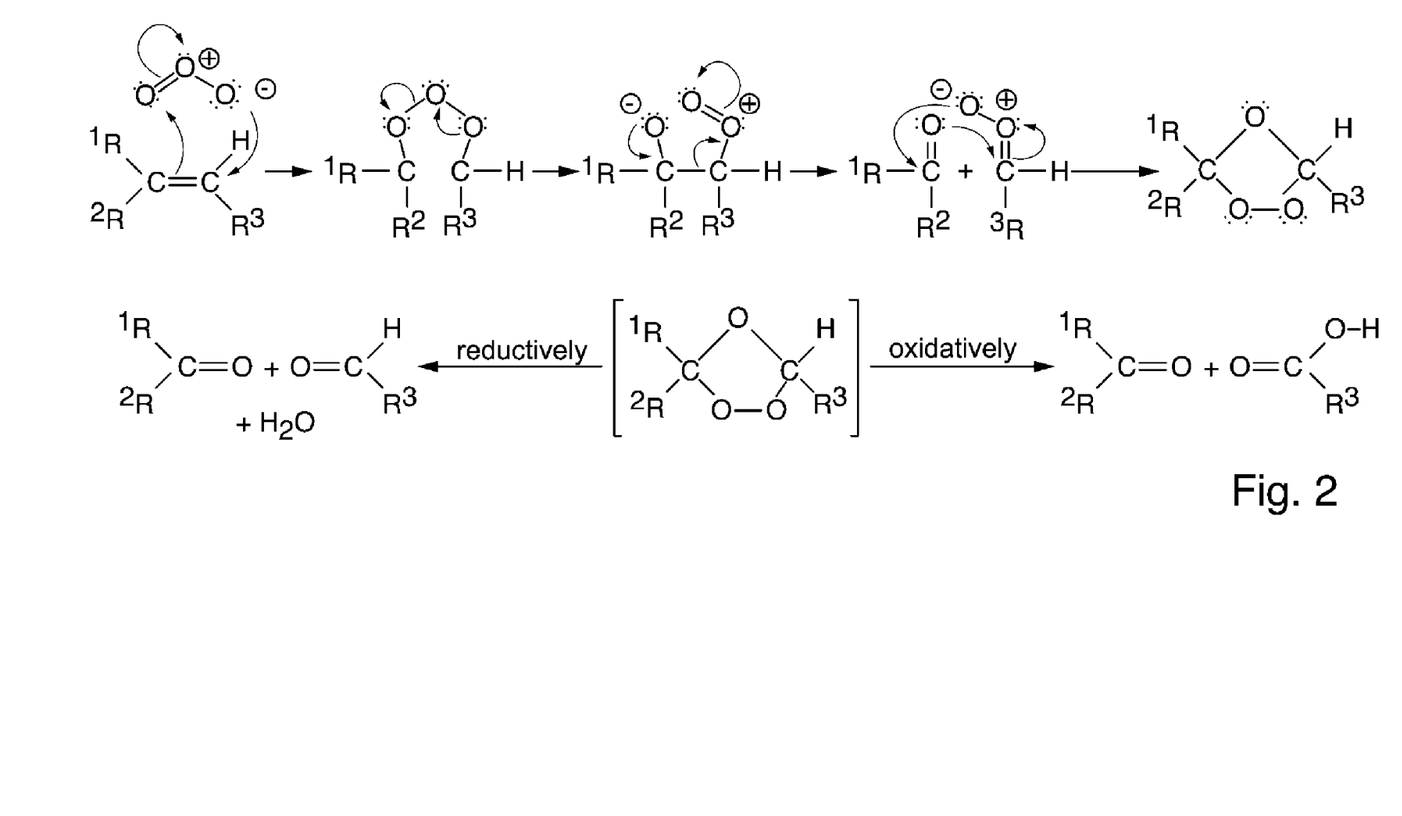
FIG. 2 illustrates a reaction scheme of a chemical reaction for binding ozone.

Suitable ozone binders may be, as a non-limiting example, unsaturated compounds, such as alkenes or alkynes, in combination with a reducing substance, for example a metal, such as zinc or iron, in particular in powder form, dimethyl sulfoxide (DMSO), or alternatively in combination with an oxidizing substance, for example a peroxide, such as $H_2O_2$. The ozone is preferably bound irreversibly. An example of the binding of ozone by means of an alkene is shown in FIG. 2 as a reaction scheme. In a first step, the alkene reacts with ozone to form an ozonide. Using a reducing agent, such as Zn powder, the ozonide can be processed reductively to form ketones and/or aldehydes. Alternatively, the ozonide can be processed oxidatively by means of an oxidizing agent, such as $H_2O_2$, to form a ketone or aldehyde and a carboxylic acid.

Suitable ozone converters can be, as a non-limiting example, hydroxide ions in a buffer solution or in an optionally liquid-impregnated or swollen polymer having alkaline units. These alkaline units react with ozone according to the following reaction equations:

$$O_3 + OH^- \rightarrow HO_2^- + O_2$$

$$2O_3 + HO_2^- \rightarrow {}^{\cdot}OH + O_2^{\cdot-} + O_2$$

Radicals formed during ozone conversion can react with added radical scavengers so that one $O_3$ molecule used results in one $O_2$ molecule.

Other alternatively suitable ozone converters are reducing agents, such as thiols. Halide or pseudohalide salts can also serve as ozone converters. For example, ozone can react in a saline solution to form sodium hypochlorite with release of oxygen:

$$NaCl + O_3 \rightarrow NaClO + O_2$$

It is also possible to use enzymes as ozone converters, for example superoxide dismutase (SOD) containing Cu or Zn.

In addition to the ozone binder and ozone converter, the first compartment 12 and the second compartment 13, respectively, may also contain further substances, for example:

metal oxides (alkali oxides, alkaline earth oxides, earth metal oxides, and subgroup metal oxides);

metals (e.g., precious metals); and activated carbon, graphene, graphene oxide, graphite, zeolite, metal organic frameworks (MOF), zeolitic imidazolate frameworks (ZIF), zeolite-like metal organic frameworks (ZMOF), Aerosil, acidic or alkaline alumina. These further substances can serve as catalysts and/or adsorbents that initiate and/or catalyze the desired reactions of the ozone.

Furthermore, the first and second compartments 12, 13 may contain a polymer having amine groups. The amine groups can serve as aldehyde binders and, depending on their structure, also as radical scavengers. As alternative or additional radical scavengers, the first and/or the second compartment may also contain redox components, i.e., substances or functional groups which are capable of reversibly donating or accepting electrons, or substances having unsaturated alkyl groups.

For the purpose of pH buffering, the first and/or the second compartment 12, 13 can also contain polymers with pH-buffering functional groups and/or with redox groups, i.e., functional groups capable of donating or accepting electrons.

On the side adjacent the measured medium, the membrane 7 can advantageously have one or more protective layers which, during operation of the measuring arrangement 10, are arranged between the measured medium and the indicator layer 18 of the membrane 7 comprising the oxygen indicator. These protective layers can be designed, for example, as layers of the membrane 7. However, they can also be designed as coatings which are arranged on or in the compartments 12, 13 and which can be arranged between the membrane 7 and the compartments 12, 13 or on the side 15 of the capsule 14 facing the medium.

One or more such protective layers can be designed as barrier layers to prevent reactive substances, in particular free chlorine or bromine, from reaching the first and second sensor surfaces 17.1, 17.2. Since the fluorescence of more common oxygen indicators is also influenced by such reactive substances, reactive substances present at the sensor surfaces 17.1, 17.2, such as chlorine or bromine, can cause corruption of the first and second measurement signals. By the barrier layer keeping these substances away from the sensor surfaces 17.1, 17.2, aging or fading of the indicator layer 18 can also be delayed. The desired barrier effect can be achieved on the one hand by one or more protective layers having a low permeability to free chlorine or bromine, on the other hand by the one or more protective layers comprising pH-buffering components which adjust a pH value higher than 7, in particular higher than 9.

Suitable as barrier layers are layers of a polymer or polymer mixture, for example selected from polystyrene, polyvinyl chloride, polyalkyl methacrylate, in particular polymethyl methacrylate, silica gels, sol gels, hydrogels, polyurethane, polytetrahydrofuran, polytetrafluoroethylene, polyester, polybutadiene, polyvinyl butyral, polyethyl acrylate, ethyl cellulose, cellulose triacetate, cellulose acetyl butyrate, polysulfones, polysulfides, silicones, fluorinated silicones. Optionally, the barrier layer may comprise a plasticizer.

A pH-buffering barrier layer for adjusting a pH value in the range above 7 may comprise a pH buffer from the series carbonates, phosphates, borates, trisodium citrate, magnesium citrate, sodium lactate, sodium acetate, potassium acetate, sodium tetraborate, potassium or sodium tartrate, sodium carbonate, potassium carbonate, sodium hydrogen carbonate, ammonium malate, di sodium malate, monosodium malate, monopotassium malate, alkali monophosphate, calcium monohydrogen phosphate, magnesium monohydrogen phosphate, and mixtures thereof. The buffer salts can be used as a solution or be present in a dry form in a matrix. Also suitable are sol-gel-based or acrylamide-based gels with buffering groups, such as those used in gel electrophoresis. Also suitable as constituents of a buffer layer are polymer buffers from the series imidazole, azoles, tetrazoles, secondary, tertiary or quaternary amines, BIS-TRIS, N-(2-hydroxyethyl)piperazine-N-2-ethane sulfonic acid (HEPES), 2-(N-morpholino)ethane sulfonic acid (MES), 3-(N-morpholino)propane sulfonic acid (MOPS), piperazine, N,N'-bis(ethane sulfonic acid), tricine, TRIS (hydroxymethyl) methylamine, or mixtures with other groups, such as carboxylic acid, phosphoric acid, sulfonic acid and their derivatives. The groups may be embedded in a polymer matrix. Also suitable are poly(beta-aminosulfonamides), amphiphilic block polymers, polyethyleneimines or polymers which form self-healing hydrogels into which can also be incorporated buffering substances.

Furthermore, the membrane 7 may comprise a barrier layer for ionic components, for example a polymer layer of a hydrophobic or superhydrophobic polymer, said layer having pores. Due to the hydrophobicity of the polymer, an aqueous solution containing ions does not enter the pores so that the pores of the polymer layer are not passable for ions. Suitable materials are, for example, hydrophobic polyvinylidene difluoride (PVDF) or silicone with fluorinated side chains. Oxygen molecules, on the other hand, are able to diffuse through the pores.

Figure 3:
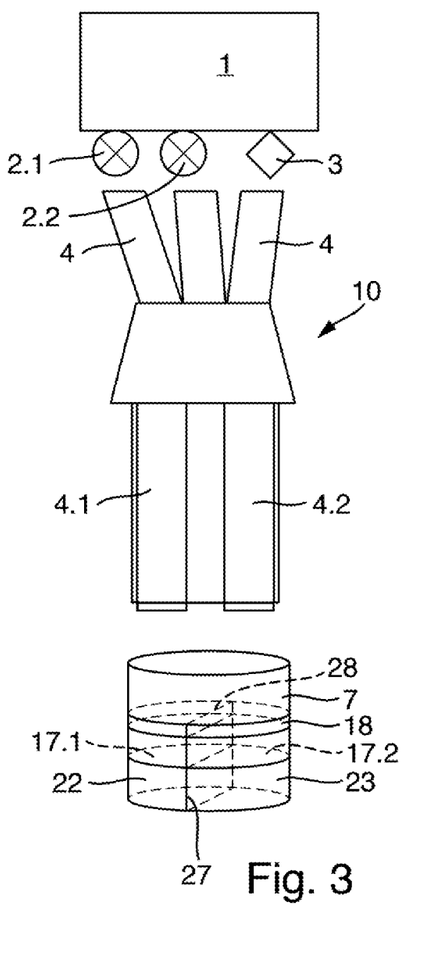
FIG. 3 shows a schematic representation of components of a measuring arrangement for measuring an ozone concentration in a measured medium according to a further exemplary embodiment.

FIG. 3 schematically shows a second exemplary embodiment of a measuring arrangement 10 for measuring an ozone concentration in a measured medium. Like the measuring arrangement 10 of the first exemplary embodiment shown in FIG. 1, the measuring arrangement 10 of this second exemplary embodiment includes a measuring circuit 1, a first light source 2.1 connected to the measuring circuit 1, a second light source 2.2 connected to the measuring circuit 1, a light receiver 3 connected to the measuring circuit 1, a membrane 7 having an indicator layer 18 containing an oxygen indicator, and optical waveguides 4, 4.1, 4.2. These components can be designed identically as described above with reference to FIG. 1 in connection with the first exemplary embodiment.

The membrane 7 has a front surface which faces away from the light-source side and which faces the measured medium during intended operation. This surface is subdivided into a first sensor surface 17.1 and a second sensor surface 17.2. Over a part of their layers, including the indicator layer 18, facing the measured medium, the membrane 7 is subdivided into two regions which are hermetically separated from one another by means of a separator 28 of a chemically inert polymer material, for example PVDF or polytetrafluoroethylene (PTFE). A first of these regions adjoins the first sensor surface 17.1, i.e., it is located in the membrane below the first sensor surface 17.1. A second of these regions adjoins the second sensor surface 17.2, i.e., it is located below the second sensor surface 17.2. The first sensor surface 17.1 is covered by a first cover element 22 taking the form of a coating in this exemplary embodiment. The second sensor surface 17.2 is covered by a second cover element 23 likewise taking the form of a coating. The coating forming the first cover element 22 includes an ozone binder, while the second cover element 23 includes an ozone converter. The ozone binder and the ozone converter can in each case be one of the substances specified in connection with the first exemplary embodiment. The ozone binder and the ozone converter may be immobilized in the coating. For example, the first cover element 22 and the second cover element 23 may in each case include a polymer layer, wherein the ozone binder and the ozone converter respectively are embedded in the polymer layer or bound to the polymer of the polymer layer. In this embodiment, the first cover element 22 and the second cover element 23 can be separated hermetically from one another via a separator 27. In at least one embodiment, the separators 28 and 27 are arranged one above the other and run in parallel. In the exemplary embodiment in FIG. 3, the first cover element 22 and the second cover element 23 are intended to have direct contact with the measured medium.

Entirely analogously to the first exemplary embodiment, the ozone concentration in the measured medium contacting the cover elements 12 and 13 can be inferred by means of two luminescence measurements by determining and evaluating a difference between a first measured value representing the oxygen concentration present at the first sensor surface 17.1 and a second measured value representing the oxygen concentration present at the second sensor surface 17.2.

The measuring circuit 1 can be designed correspondingly identically to the measuring circuit 1 of the measuring arrangement 10 of the first exemplary embodiment described with reference to FIG. 1.

Figure 4:
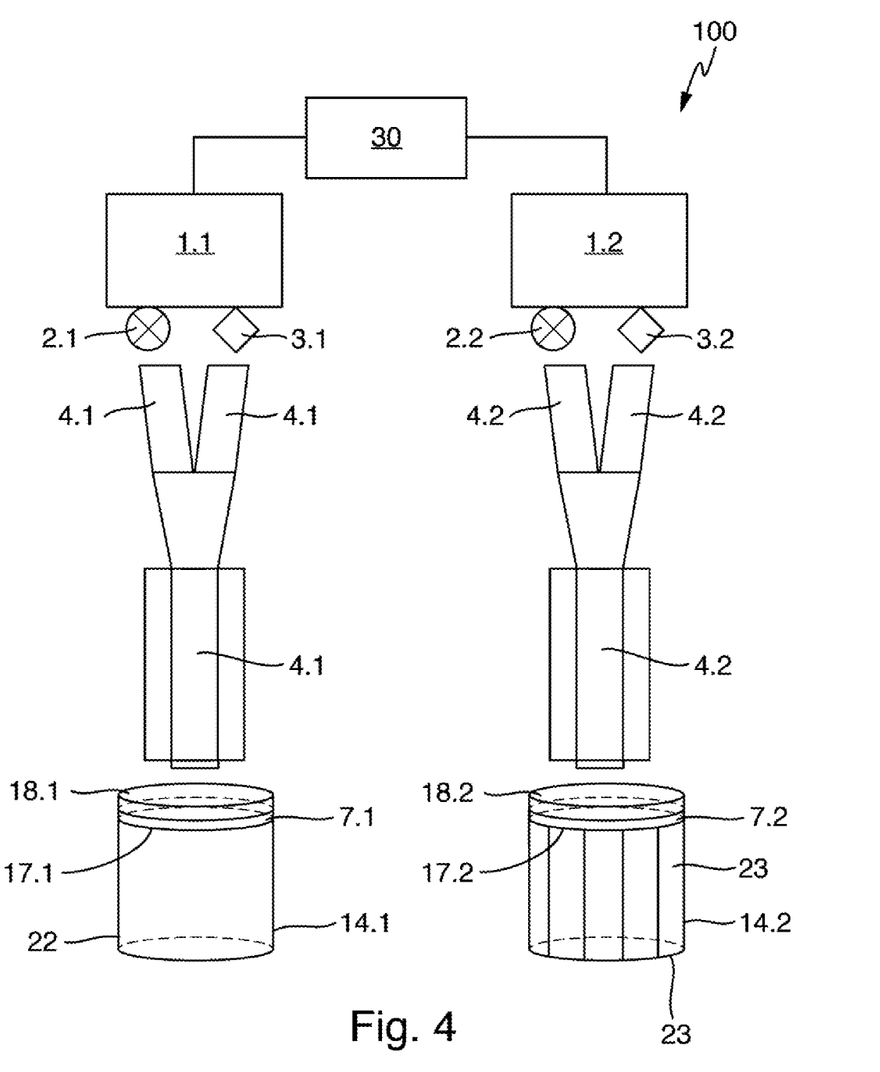
FIG. 4 shows a schematic representation of components of a measuring arrangement for measuring an ozone concentration in a measured medium according to a further exemplary embodiment.

FIG. 4 schematically shows a third exemplary embodiment of a measuring arrangement 100 for measuring an ozone concentration in a measured medium. The measuring arrangement 100 includes a first light source 2.1 and a first light receiver 3.1 as well as a first measuring circuit 1.1, which is designed to excite the first light source 2.1 to emit measuring light and to receive and process an electrical measurement signal of the first light receiver 3.1. Furthermore, the measuring arrangement 100 includes a second light source 2.2 and a second light receiver 3.2, as well as a second measuring circuit 1.2, which is designed to excite the second light source 2.2 to emit measuring light and to receive and process an electrical measurement signal of the second light receiver 3.2. In the exemplary embodiment shown in FIG. 4, the two measuring circuits 1.1 and 1.2 are connected to a higher-level evaluation circuit 30, for example an electronic unit of a measuring transducer, which receives measurement signals of the measuring circuits 1.1, 1.2 and is designed to further process these measurement signals and to determine measured values for the ozone concentration in a measured medium from the measurement signals. The measuring circuits 1.1, 1.2 and the evaluation circuit 30 can take the form of a single measuring and evaluation circuit or, as in the example shown here or in another way, can be divided into a plurality of interacting individual circuits.

The higher-level evaluation circuit 30 can, for example, be a circuit of a conventional measuring transducer of process measurement technology. This measuring transducer can comprise a housing containing input means, via which a user can input commands or parameters, as well as display means by means of which measured values or other information can be displayed. The measuring transducer can also be designed as a compact measuring transducer. In this case, the measuring transducer comprises a housing in which a transducer circuit is accommodated which processes the measurement signals and forwards them via a cable and/or by radio but in which no separate input or display means are provided. The information transmitted by cable or radio, in particular measured values, can be received, optionally processed and displayed by an external operating device, for example a portable computer, a tablet, a smart phone or another smart device.

The measuring arrangement 100 further comprises a first membrane 7.1 and a second membrane 7.2. The two membranes 7.1 and 7.2 each include indicators layer 18.1 and 18.2, respectively, containing an oxygen indicator. The membranes 7.1 and 7.2 can be designed identically to the membranes 7 of the previously described exemplary embodiments. The front surface of the first membrane 7.1 that faces the measured medium during measuring operation forms the first sensor surface 17.1 of the measuring arrangement 100; the corresponding front surface of the second membrane 7.2 forms the second sensor surface 17.2 of the measuring arrangement 100. The first sensor surface 17.1 is covered by a first cover element 22; the second sensor surface 17.2 is covered by a second cover element 23. The cover elements 22, 23 can take the form of coatings (like the cover elements 22, 23 of the second exemplary embodiment) or of capsules with liquid transfer features, entirely analogous to the compartments 12, 13 of the capsule 14 in the first exemplary embodiment (FIG. 1). In the present embodiment, the cover elements 22, 23 are designed as individual capsules 14.1, 14.2. The first capsule 14.1 contains an ozone binder; the second capsule 14.2 contains an ozone converter. The ozone binder and ozone converter can be of identical composition to the ozone binder or ozone converter of the first exemplary embodiment. In addition to the ozone binder and ozone converter, the capsules 14.1, 14.2 can contain further additives, such as already described with reference to the first exemplary embodiment. The capsules 14.1, 14.2 have liquid transfer features (not shown in FIG. 4) via which oxygen and ozone from the measured medium pass into the capsules 14.1, 14.2 and oxygen from the capsules 14.1, 14.2 reaches the sensor surfaces 17.1, 17.2.

The cover elements 22, 23 are intended for contact with the measured medium. One or more protective layers, in particular a barrier layer according to one of the embodiments described above, can be arranged between the measured medium and the first sensor surface 17.1 or between the measured medium and the second sensor surface 17.2. This (these) protective layer(s) or the barrier layer can take the form of a coating inside the capsules 14.1, 14.2 on the sides of the cover elements facing the measured medium or as a layer or layers forming part of the membrane 7.

The first light source 2.1 and the first light receiver 3.1 are connected to the first membrane 7.1 via the first optical waveguides 4.1 such that measuring light emitted by the first light source 2.1 excites to luminescence the oxygen indicator contained in the first indicator layer 18.1 of the membrane 7.1 and such that the luminescence light from the first indicator layer 18.1 reaches the first light receiver 3.1 via the first optical waveguides 4.1. Oxygen present at the first sensor surface 17.1 leads to a quenching of the luminescence of the oxygen indicator. The light receiver 3.1 is designed to convert the received luminescence light into an electrical signal and to output it to the first measuring circuit 1.1, which generates therefrom a first measurement signal which depends on an oxygen concentration present at the first sensor surface 17.1.

The second light source 2.2 and the second light receiver 3.2 are connected to the second membrane 7.2 via the second optical waveguides 4.2 such that measuring light emitted by the second light source 2.2 excites to luminescence the oxygen indicator contained in the second indicator layer 18.2 of the membrane 7.2 and such that the luminescence light from the second indicator layer 18.2 reaches the second light receiver 3.2 via the second optical waveguides 4.2. Oxygen present at the second sensor surface 17.2 leads to a quenching of the luminescence of the oxygen indicator. The light receiver 3.2 is designed to convert the received luminescence light into an electrical signal and to output it to the second measuring circuit 1.2, which generates therefrom a second measurement signal which depends on an oxygen concentration present at the second sensor surface 17.2.

The first and second measuring circuits 1.1, 1.2 are designed to output the first measurement signal and the second measurement signal to the higher-level evaluation circuit 30, which processes them.

The components illustrated in FIG. 4 can be accommodated in a single housing. The circuit 30 can be arranged at a distance from this housing and can be connected to the measuring circuits 1.1 and 1.2 via a releasable connector coupling. In an alternative embodiment, the first measuring circuit 1.1, the first light source 2.1, the first light receiver 3.1, the first optical waveguide 4.1, the first membrane 7.1 and the first capsule 14.1 can be arranged in a first housing, while the second measuring circuit 1.2, the second light source 2.2, the second light receiver 3.2, the second optical waveguide 4.2, the second membrane 7.2 and the second capsule 14.2 are accommodated in a second housing separate from the first housing.

In order to determine an ozone concentration in a measured medium, the front sides, i.e. the sides of the cover elements 22, 23 that face away from the first membrane 7.1 or the second membrane 7.2, can be brought into contact with the measured medium. Ozone and oxygen from the measured medium enter the capsules 14.1, 14.2 via the liquid transfer features and are reacted there by the ozone binder or the ozone converter in the manner already described with reference to the first exemplary embodiment so that the difference between the oxygen concentration present at the first sensor surface 17.1 and the oxygen concentration present at the second sensor surface 17.2 is a measure of the ozone concentration contained in the measured medium. By means of a first luminescence measurement, the first measuring circuit 1.1 generates a first measurement signal by exciting the first light source 2.1 to emit measuring light which excites the oxygen indicator to luminescence and by receiving a receiver signal of the light receiver 3.1 which depends on the luminescence radiation of the oxygen indicator interacting with the oxygen present at the first sensor surface 17.1. In an analogous manner, the second measuring circuit 1.2, by means of the second light source 2.2 and the second light receiver 3.2, generates a second measurement signal which depends on the oxygen concentration present at the second sensor surface 17.2. The first and second measurement signals are output to the higher-level evaluation circuit 30 and said evaluation circuit calculates and outputs a measured value of the ozone concentration on the basis of the first and second measurement signals as already described with reference to the first exemplary embodiment.

Figure 5:
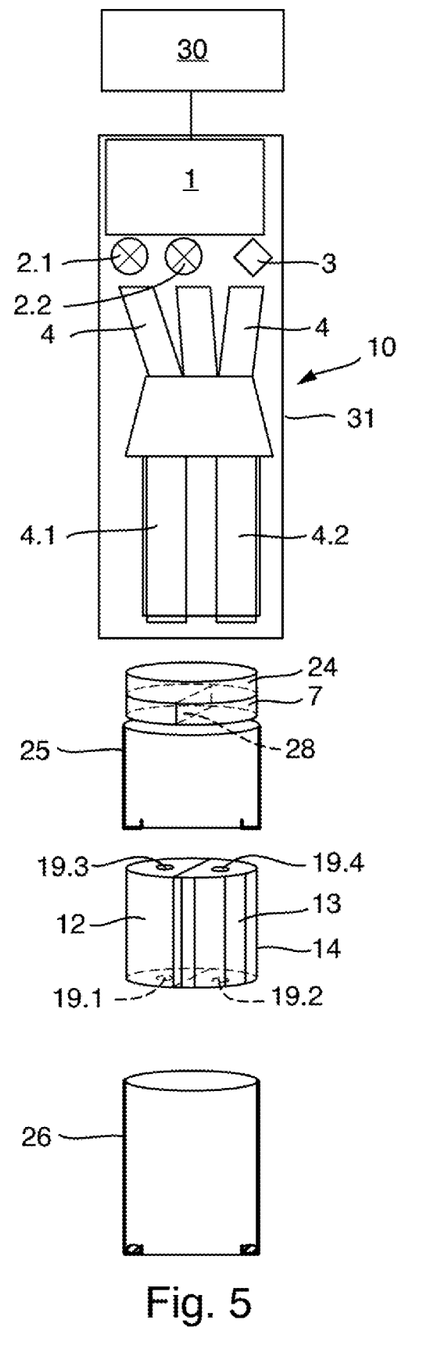
FIG. 5 shows an exploded view of a measuring arrangement for measuring an ozone concentration in a measured medium according to another exemplary embodiment.

FIG. 5 schematically shows an exploded view of a measuring arrangement 200 for measuring an ozone concentration in a measured medium according to a fourth exemplary embodiment. The basic structure of the measuring arrangement 200 corresponds to that of the first exemplary embodiment described with reference to FIG. 1. The measuring arrangement 200 includes a measuring circuit 1 which is connected to two light sources 2.1, 2.2 and a light receiver 3 and which is designed to excite the light sources 2.1, 2.2 successively, in particular alternately, to emit measuring light. The light receiver 3 is designed to convert received light into an electrical measurement signal and to output it to the measuring circuit. The measuring circuit 1 is designed to receive, process, for example amplify, and digitize the electrical measurement signal and to output it to an electronic evaluation unit 30, for example a measuring transducer or compact measuring transducer connected to the measuring circuit 1, for further processing, for example for determining a measured ozone value according to the method already described above. Alternatively, the measuring circuit 1 itself can be designed to determine a measured ozone value from the measurement signals of the light receiver. In this case, it can be designed to output the determined measured ozone value to the higher-level electronic evaluation unit 30.

The measuring arrangement 24 includes a membrane 7 including at least one indicator layer (not shown in FIG. 5) with an oxygen indicator. The membrane 7 can be designed entirely analogously to the membrane 7 described in the previous exemplary embodiments. It may be divided over its full height by a separator 28 into two regions which are hermetically separated from one another. The membrane 7 is applied to a substrate 24 which is transparent to the measuring light and to the luminescence light emitted by the oxygen indicator. The substrate 24 serves to stabilize the membrane 7.

Measuring light emitted by the light source 2 is guided onto the membrane 7 by means of a bundle of optical waveguides 4. Luminescence light of the oxygen indicator is conducted from the optical waveguides 4 to the light receiver 3.

Figure 6A:
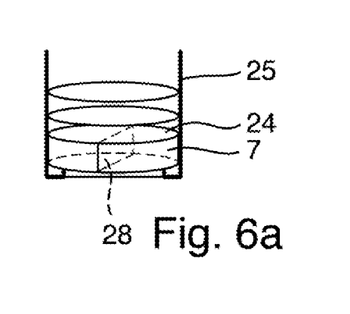
FIG. 6a shows the membrane of the measuring arrangement according to FIG. 5 arranged in a replaceable cap.

The measuring circuit 1, the light source 2, the light receiver 3 and the optical waveguides 4 are arranged in a housing 31, for example a cylindrical housing, which can have at its front end facing the membrane 7 an opening or a window which is transparent to the measuring light and the luminescence light. The membrane 7 applied to the substrate 24 is arranged in a first cap 25 which can be detachably connected to the housing 31, for example by means of a threaded connection. The membrane 7 arranged with the substrate 24 in the capsule 15 is shown in a detailed view in FIG. 6a. The cap 25 is replaceable so that the membrane 7 can be exchanged for a new membrane 7 as needed.

The front side of the membrane 7 that faces the measured medium during measuring operation of the measuring arrangement 200 is covered by a capsule 14 which, for example, can be designed identically to the capsule 14 of the measuring arrangement 10 of the first exemplary embodiment (FIG. 1). The capsule 14 is divided into a first compartment 12 and a second compartment 13. As with first cover element 22, the first compartment 12 covers a first sensor surface 17.1 of the membrane 7. As with second cover element 23, the second compartment 13 covers a second sensor surface 17.2 of the membrane 7. The first compartment 12 contains an ozone binder; the second compartment 13 contains an ozone converter. Substances which are suitable as ozone binders and ozone converters are the same as the substances mentioned in connection with the first exemplary embodiment (FIG. 1).

As in the first exemplary embodiment, the capsule 14 has liquid transfer features 19.1, 19.2, 19.3 and 19.4 in its front and rear walls so that oxygen and ozone from a measured medium contacting the front side of the capsule 14 can enter the first compartment 12 via the liquid transfer feature 19.1 and the second compartment 13 via the liquid transfer feature 19.2. In the first compartment 12, ozone is bound; in the second compartment 13, ozone is chemically converted into oxygen. Oxygen from the first compartment 12 passes via the liquid transfer feature 19.3 to the first sensor surface 17.1 of the membrane 7; oxygen from the second compartment passes correspondingly via the liquid transfer feature 19.4 to the second sensor surface 17.2. The oxygen concentrations present at the sensor surfaces 17.1 and 17.2 can be detected in the manner already described by means of luminescence measurements and an ozone concentration in the measured medium can be determined therefrom as described.

Figure 6B:
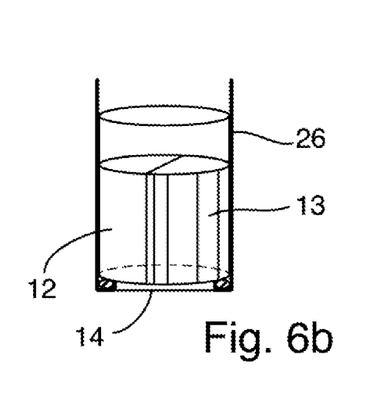
FIG. 6b shows the capsule of the measuring arrangement according to FIG. 5 arranged in a replaceable cap.

In the exemplary embodiment of FIG. 5, the capsule 14 is connected to the housing 31 by means of a second cap 26. For this purpose, the capsule 14 is accommodated in the second cap 26 which, on its front side facing away from the housing 31, has an opening through which a measured medium can come into contact with the front side of the capsule 14 and the liquid transfer features 19.1, 19.2. On the rear side, the second cap 26 can be detachably connected, for example by means of a threaded connection, to the housing 31 or, in an alternative embodiment, to the first cap 25. The unit which consists of the capsule 14 and cap 26 and which is designed to connect to the housing 31 is shown in FIG. 6b.

In an alternative exemplary embodiment, a single cap can be provided which can be detachably connected to the housing 31 and in which are arranged the membrane 7, an optionally present substrate 24 and the cover elements upstream of the membrane, for example in the form of coatings of the sensor surfaces of the membrane or in the form of compartments of a capsule 14. The capsule can be designed analogously to the second capsule 26 shown in FIG. 6b. In particular, it can have a front opening through which a measured medium can come into contact with the front side of the cover elements.

In a further alternative exemplary embodiment, the individual components of the measuring arrangement 10 shown in FIG. 1 or 3 can be connected permanently, i.e. inseparably, to one another in a single unit. In this case, the measuring arrangement 10 can be used as a disposable sensor.

The invention claimed is:

1. A measuring arrangement for measuring an ozone content in a measured medium, the measuring arrangement comprising:
   a first sensor surface and a second sensor surface;
   a first cover element adjacent the first sensor surface and including an ozone binder substance that binds ozone without releasing oxygen or any species further reacting to form oxygen, wherein a side of the first cover element facing away from the first sensor surface is adapted to contact the measured medium, and wherein the first cover element is permeable at least to oxygen;
   a second cover element adjacent the second sensor surface and including an ozone converter substance that reacts with ozone to form oxygen, wherein a side of the second cover element facing away from the second sensor surface is adapted to contact the measured medium, and wherein the second cover element is permeable at least to oxygen;
   a measuring sensor configured to generate a first measurement signal dependent on a first oxygen concentration present at the first sensor surface and a second measurement signal dependent on a second oxygen concentration present at the second sensor surface; and
   an electronic evaluation unit configured to determine a value of a measured variable representing the ozone content in the measured medium based on the first measurement signal and second measurement signal.

2. The measuring arrangement of claim 1, wherein the measuring sensor comprises:
   light source and a second light source;
   a light receiver;
   a membrane including the first sensor surface and the second sensor surface and in which an oxygen indicator substance is immobilized; and
   optical waveguides connecting the first light source and the light receiver to a region of the membrane covered by the first sensor surface, the optical waveguides further connecting the second light source and the light receiver to a region of the membrane covered by the second sensor surface,
   wherein the light receiver is configured to convert light received via the optical waveguides into electrical signals, and wherein the measuring sensor further comprises a measuring circuit configured to generate the first measurement signal and the second measurement signal from the electrical signals from the light receiver.

3. The measuring arrangement of claim 1, wherein the measuring sensor comprises:
a light source;
a first light receiver and a second light receiver;
a membrane including the first sensor surface and the second sensor surface and in which an oxygen indicator substance is immobilized; and
optical waveguides connecting the light source and the first light receiver to a region of the membrane covered by the first sensor surface, the optical waveguides further connecting the light source and the second light receiver to a region of the membrane covered by the second sensor surface,
wherein the first light receiver and the second light receiver are each configured to convert light received via the optical waveguides into electrical signals, and wherein the measuring sensor includes a measuring circuit configured to generate the first measurement signal and the second measurement signal from the electrical signals from the first light receiver and second light receiver, respectively.

4. The measuring arrangement of claim 1, wherein the measuring sensor comprises:
a light source;
a light receiver;
a first membrane including the first sensor surface and a second membrane including the second sensor surface, wherein an oxygen indicator substance is immobilized in the first membrane and in the second membrane;
one or more first optical waveguides connecting the light source and the light receiver to the first membrane; and
one or more second optical waveguides connecting the light source and the light receiver to the second membrane,
wherein the light receiver is configured to convert light received via the first optical waveguides and second optical waveguides into electrical signals, and wherein the measuring sensor includes a measuring circuit configured to generate the first measurement signal and the second measurement signal from the electrical signals from the light receiver.

5. The measuring arrangement of claim 1, wherein the measuring sensor comprises:
a first light source and a second light source;
a first light receiver and a second light receiver;
a first membrane including the first sensor surface and a second membrane including the second sensor surface, wherein an oxygen indicator substance is immobilized in the first membrane and in the second membrane;
one or more first optical waveguides connecting the first light source and the first light receiver to the first membrane; and
one or more second optical waveguides connecting the second light source and the second light receiver to the second membrane.

6. The measuring arrangement of claim 5, wherein:
the first light receiver is adapted to convert light received via the one or more first optical waveguides into first electrical signals;
the second light receiver is adapted to convert light received via the one or more second optical waveguides into second electrical signals; and
the measuring sensor includes a measuring circuit configured to generate the first measurement signal from the first electrical signals and the second measurement signal from the second electrical signals.

7. The measuring arrangement of claim 1, wherein the measuring sensor comprises:
a first membrane including the first sensor surface and a second membrane including the second sensor surface, wherein the first membrane and second membrane are permeable to oxygen;
a first electrolyte chamber, which is at least partial enclosed by the first membrane and filled with a first electrolyte, in which a first working electrode and a first counter electrode are arranged;
a second electrolyte chamber, which is at least partial enclosed by the second membrane and filled with a second electrolyte, in which a second working electrode and a second counter electrode are arranged; and
a measuring circuit configured to generate:
first electrical signals representative of a current passing through the first electrolyte at a first polarization voltage applied between the first working electrode and the first counter electrode;
the first measurement signal from the first electrical signals;
second electrical signals representative of a current passing through the second electrolyte at a second polarization voltage applied between the second working electrode and the second counter electrode; and
the second measurement signal from the second electrical signals.

8. The measuring arrangement of claim 1, wherein the first cover element is a layer disposed adjacent the first sensor surface, and the second cover element is a layer disposed adjacent the second sensor surface.

9. The measuring arrangement of claim 1, wherein the first cover element is a detachable capsule disposed upstream of the first sensor surface or a compartment of a capsule, the compartment adjacent the first sensor surface, and
wherein the second cover element is a detachable capsule disposed upstream of the second sensor surface or a compartment of a capsule, the compartment adjacent the second sensor surface.

10. The measuring arrangement of claim 9, wherein the capsule includes a compartment containing the ozone binder and/or a compartment containing an ozone scavenger, wherein the compartment or each compartment has a media-contacting front wall and a rear wall contacting the first sensor surface and/or the second sensor surface, and wherein the front wall and the rear wall have a liquid transfer feature.

11. The measuring arrangement of claim 10, wherein the liquid transfer feature includes a fiber diaphragm, a ceramic diaphragm, a gap, a cut, or a fluid-permeable, organic or inorganic membrane.

12. The measuring arrangement of claim 9, wherein the capsule is accommodated in a cap detachably connected to a housing part of the measuring sensor.

13. The measuring arrangement of claim 1, wherein the ozone binder includes at least one unsaturated compound, which forms an ozonide with ozone, and a reagent for the oxidative or reductive preparation of the formed ozonide.

14. The measuring arrangement of claim 1, wherein the ozone converter includes an alkaline buffer, buffered solid electrolyte, a reducing agent, a salt that reacts with ozone to form oxygen, or an enzyme.

15. The measuring arrangement of claim 1, wherein the first cover element further includes an aldehyde binder.

16. The measuring arrangement of claim 1, wherein the second cover element further includes a radical scavenger.

17. A method for measuring an ozone content in a measured medium, the method comprising:
- providing the measuring arrangement according to claim 1;
- bringing the first sensor surface covered by the first cover element into contact with the measured medium;
- bringing the second sensor surface covered by the second cover element into contact with the measured medium;
- converting ozone entering the second cover element from the measured medium into oxygen via a chemical reaction with the ozone converter contained in the second cover element;
- binding ozone entering the first cover element from the measured medium to the ozone binder contained in the first cover element;
- detecting the first measurement signal dependent on the first oxygen concentration present at the first sensor surface;
- detecting the second measurement signal dependent on the second oxygen concentration present at the second sensor surface; and
- determining from the first and the second measurement signals a measured value of the ozone content in the measured medium using the evaluation unit.

18. The method of claim 17, wherein determining the measured value includes:
- determining from the first measurement signal a first measured value representing the first oxygen concentration at the first sensor surface;
- determining from the second measurement signal a second measured value representing the second oxygen concentration at the second sensor surface; and
- determining the measured value from a difference between the first measured value and second measured value.

* * * * *